United States Patent [19]

Rolando et al.

[11] Patent Number: 5,364,907
[45] Date of Patent: Nov. 15, 1994

[54] GRAFT COPOLYMERS AND GRAFT COPOLYMER/PROTEIN COMPOSITIONS

[75] Inventors: Richard J. Rolando, Oakdale; Patrick L. Coleman, Minneapolis; Steven L. Kangas, Woodbury; Thomas A. Kotnour, Faribault, all of Minn.

[73] Assignee: Minnesota Mining and Manufacturing Company, St. Paul, Minn.

[21] Appl. No.: 71,327

[22] Filed: Jun. 2, 1993

Related U.S. Application Data

[63] Continuation of Ser. No. 595,275, Oct. 10, 1990, abandoned.

[51] Int. Cl.$^5$ .............. C08G 63/48; C08G 63/91; G08L 9/00; G08L 47/00
[52] U.S. Cl. .............. 525/54.1; 525/69; 525/87; 525/193; 525/204; 525/240; 525/241; 525/242; 525/243; 525/244; 525/260; 525/263; 525/265; 525/327.9; 525/333.3; 525/333.6; 525/375; 525/435; 525/525; 525/530; 435/188; 530/403; 530/812; 530/815; 530/816
[58] Field of Search .............. 525/54.1, 69, 87, 193, 525/204, 240, 241, 242, 243, 244, 260, 263, 265, 327.9, 333.3, 333.6, 375, 435, 525, 530; 435/188; 530/402, 403, 811, 812, 815, 816

[56] References Cited

U.S. PATENT DOCUMENTS

| | | | |
|---|---|---|---|
| 3,177,270 | 4/1965 | Jones et al. | 525/263 |
| 3,880,580 | 4/1975 | Horowitz et al. | 525/333.9 |
| 4,003,874 | 1/1977 | Ide et al. | 523/219 |
| 4,146,529 | 3/1979 | Yamamoto et al. | 524/262 |
| 4,210,418 | 7/1980 | Brown et al. | 435/7.4 |
| 4,228,255 | 10/1980 | Fujimoto et al. | 525/288 |
| 4,311,573 | 1/1982 | Mayhan et al. | 525/262 |
| 4,497,899 | 2/1985 | Armstrong et al. | 435/7.36 |
| 4,497,900 | 2/1985 | Abram et al. | 435/7.36 |
| 4,675,361 | 6/1987 | Ward, Jr. | 525/92 |
| 4,844,966 | 7/1989 | Calenoff et al. | 435/7.94 |
| 4,845,132 | 7/1989 | Masuoka et al. | 525/329.4 |
| 4,897,433 | 1/1990 | Sugo et al. | 522/116 |
| 4,902,749 | 2/1990 | Akkapeddi et al. | 525/66 |
| 4,945,146 | 7/1990 | Kapmeyer et al. | 526/304 |
| 5,013,795 | 5/1991 | Coleman et al. | 525/279 |

FOREIGN PATENT DOCUMENTS

| | | |
|---|---|---|
| 0234083 | 9/1987 | European Pat. Off. |
| 86-302861 | 3/1985 | Japan |
| 0105625 | 4/1988 | Japan |
| 89-367670 | 4/1988 | Japan |
| 1393693 | 5/1975 | United Kingdom |

OTHER PUBLICATIONS

Plastics Compounding, Jan./Feb. 1986, pp. 44–53 (Eise et al.).
Plastics Compounding, Sep./Oct. 1986, pp. 24–39 (Frund et al.).
Polymer Prep., 1986, 27, 89 (Sahar).
Biomedical Applns. of Immobilized Enzymes, vol. 2, T. M. S. Chang, Ed. Plenum Publishing Corp., (Engvall).
Clin. Chem. 1976, 22, 1243 (Wisdom).
J. Colloid and Interface Sci. 1985, 106, 438 (Lavielle et al.).

*Primary Examiner*—Nathan M. Nutter
*Attorney, Agent, or Firm*—Gary L. Griswold; Walter N. Kirn; Paul W. Busse

[57] ABSTRACT

Graft copolymers comprising a poly-alpha-olefin base polymer selected from the group consisting of polyethylene, polypropylene, polystyrene, and compatible mixtures thereof, having grafted thereto an olefinic monomer. The grafted monomer is present in an amount effective to increase the amount of protein that will bind to the graft copolymer as compared with the base polymer.

Also disclosed are polymer/protein compositions comprising a graft copolymer having a protein immobilized on the surface thereof, processes for the preparation of the above-described graft copolymers and compositions, methods of immobilizing proteins, and methods of immunoassay based on such immobilization.

8 Claims, 1 Drawing Sheet

5,364,907

GRAFT COPOLYMERS AND GRAFT COPOLYMER/PROTEIN COMPOSITIONS

This application is a continuation of U.S. Patent application Ser. No. 07/595,275 filed Oct. 10, 1990, now abandoned.

BACKGROUND OF THE INVENTION

1. Technical Field

This invention relates to graft copolymers and processes for their preparation. In another aspect, this invention relates to immobilization of proteins on synthetic polymers and also to methods of immunoassay based on such immobilization. This invention also relates to polymers with proteins immobilized on the surface thereof.

2. Description of the Related Art

Processing and/or production of polymers using wiped-surface reactors such as screw extruders and twin-screw extruders is well known (such processing is often referred to as reactive extrusion). Twin-screw extruders and their use in continuous processes such as graft polymerization, alloying, bulk polymerization of vinyl monomers, and condensation and addition reactions are generally described in *Plastics Compounding*, January/February 1986, pp. 44–53 (Else et al.) and *Plastics Compounding*, September/October 1986, pp. 24–39 (Frund et al.). Graft reactions are said to be carried out by first melting a polymeric species in the initial stages of an extruder, injecting a peroxide catalyst into the extruder, and mixing in a monomer under high shear conditions. Advantages of the twin-screw extrusion process are said to include narrow distribution of molecular weight, improved melt-flow properties, consistent process control, and continuous processing.

Graft polymerization reactions of polyolefins with various monomers using wiped-surface reactors are known. Such grafting is said to be useful in providing a polymer adduct with functionality to allow further modification of structure and properties, and general mechanistic proposals regarding the formation of these "mechanochemically synthesized" adducts are discussed in connection with the grafting of maleic anhydride onto polypropylene in *Polymer Prep.*, 1986, 27, 89 (Al-Malaika). Particular free radical graft polymerization reactions have been reported. For example, U.S. Pat. No. 3,177,270 (Jones et al.) discloses a process of preparing graft copolymers by malaxing an olefin polymer at a temperature between 110° C. and 250° C. while contacting the polymer with a minor proportion of a mixture comprising a monovinyl aromatic compound and optionally one or more other monomers such as acrylic acid, methacrylic acid, acrylonitrile, methyl methacrylate, methacrylonitrile, or maleic anhydride, the mixture having dissolved therein an organic peroxide. British Pat. No. 1,393,693 (Steinkamp et al.) discloses the use of a single-screw extruder to graft monomers such as maleic anhydride and acrylic acid onto polyolefins such as polypropylene in the presence of a suitable free radical initiator such as an organic peroxide. The product graft copolymers are said to have a melt flow rate (MFR) of at least 50% greater than the MFR of the base polymer.

U.S. Pat. No. 4,003,874 (Ide et al.) discloses modified polyolefins obtained by adding an unsaturated carboxylic acid or an anhydride thereof and an organic peroxide to a polyolefin and melting these components in an extruder. The polyolefin so obtained adheres to glass fibers.

U.S. Pat. No. 4,146,529 (Yamamoto et al.) discloses a process for the production of modified polyolefins by combining a polyolefin with one or more carboxylic acids or their anhydrides in the presence of a radical producing agent in an extruder and in the presence of an organosilane.

U.S. Pat. No. 4,228,255 (Fujimoto et al.) discloses a method for crosslinking a polyolefin, the polyolefin being a low density polyethylene or a polyolefin mixture containing a low density polyethylene, comprising reacting the polyolefin with an organic silane and an organic free radical initiator to form a silane-grafted polyolefin, then mixing the silane-grafted polyolefin with a silanol condensation catalyst. The mixture is extruded with heating in a single-screw extruder to obtain a crosslinked polyethylene.

Among the myriad properties of some synthetic polymers is their ability to reversibly bind proteins. Many techniques for assay of protein-containing substrates are based on such binding. Enzyme linked immunosorbent assay, described in "Biomedical Applications of Immobilized Enzymes", Vol. 2, T. M. S. Chang, Ed. Plenum Publishing Corp., (Engvall) is but one such technique. ELISA and other enzyme immunoassay techniques such as those described in *Clin. Chem.* 1976, 22, 1243 (Wisdom) generally use a material such as glass, polycarbonate, or polystyrene as a solid-phase immune adsorbent, which immobilizes one member of an immunological pair. The subsequent assay relies on competitive binding of the other member of the immunological pair in labeled and unlabeled form, to the immobilized member. One recognized disadvantage of the use of such techniques is that the immobilized protein is only physically adsorbed to the immune adsorbent such that adsorbed protein can be washed off to various degrees by rinsing or contact with aqueous buffer solutions. A decrease in assay accuracy, precision, and sensitivity can result from such "leakage" of the adsorbed protein.

SUMMARY OF THE INVENTION

This invention provides graft copolymers comprising a poly-alpha-olefin base polymer selected from the group consisting of polyethylene, polypropylene, polystyrene, and a compatible mixture of any two or more thereof, having grafted thereto an olefinic monomer selected from the group consisting of: in the instance of a polyethylene base polymer, 1-vinylimidazole, polyethylene-glycol monomethacrylate, and N-vinylpyrrolidone, and a mixture of any two or more thereof; in the instance of a polypropylene base polymer, 1-vinylimidazole; in the instance of a polystyrene base polymer, 1-vinylimidazole; and in the instance of a base polymer mixture of any two or more of polyethylene, polypropylene, and polystyrene, 1-vinylimidazole;

the grafted monomer being present in an amount effective to increase the amount of protein that will bind to the graft copolymer as compared with the base polymer.

This invention also provides a polymer/protein composition comprising: a graft copolymer that comprises a poly-alpha-olefin base polymer selected from the group consisting of polyethylene, polypropylene, polystyrene, and a compatible mixture of any two or more thereof, having grafted thereto an olefinic monomer selected from the group consisting of: in the instance of a polyethylene base polymer, 1-vinylimidazole, hydroxyethyl methacrylate, N,N-dimethylacrylamide, polyethyleneglycol monomethacrylate, N-vinylpyrrolidone, and a mixture of any two or more thereof; in the instance of a polypropylene base polymer, 1-vinylimidazole; in the instance of a polystyrene base polymer, 1-vinylimidazole; and in the instance of a base polymer mixture of any two or more of polyethylene, polypropylene, and polystyrene, 1-vinylimidazole; the grafted monomer being present in an amount effective to increase the amount of protein that will bind to the graft copolymer as compared with the base polymer, with a protein immobilized on the surface of said composition.

This invention also provides processes for preparing the graft copolymers described above. One such process comprises the steps of:
1) feeding to a reactor materials comprising
   (a) the poly-alpha-olefin base polymer
   (b) an effective amount of a free radical initiator system comprising one or more free radical initiators; and
   (c) the olefinic monomer; wherein all materials are substantially free of oxygen;
2) reacting the materials in the reactor to provide a graft copolymer as described above; and
3) withdrawing the graft copolymer from the reactor.

This invention also provides a method of immobilizing a protein, comprising the step of:
contacting the protein with a graft copolymer surface, wherein the graft copolymer comprises a poly-alpha-olefin base polymer selected from the group consisting of polyethylene, polypropylene, polystyrene, and a compatible mixture of any two or more thereof, having grafted thereto an olefinic monomer selected from the group consisting of: in the instance of a polyethylene base polymer, 1-vinylimidazole, hydroxyethyl methacrylate, N,N-dimethylacrylamide, polyethyleneglycol monomethacrylate, N-vinylpyrrolidone, and a mixture of any two or more thereof; in the instance of a polypropylene base polymer, 1-vinylimidazole; in the instance of a polystyrene base polymer, 1-vinylimidazole; and in the instance of a base polymer mixture of any two or more of polyethylene, polypropylene, and polystyrene, 1-vinylimidazole, the grafted monomer being present in an amount effective to increase the amount of protein that will bind to the graft copolymer as compared with the base polymer, at a temperature and for a time sufficient to cause the protein to become immobilized on the surface.

Further, the invention provides a method of immunoassay comprising the steps of:
1) treating an article comprising a surface of a polymer/protein composition as described above with one member of an immunological pair;
2) incubating the treated article with a solution suspected of containing the second member of the immunological pair; and
3) determining the amount of the second member of the immunological pair present in the solution.

By virtue of the grafted monomers, graft copolymers of the invention provide an increased amount of irreversible binding (i.e., immobilizing) of proteins for the purposes of, e.g., immunoassay. Accordingly, graft copolymer/protein compositions of the invention allow improvement in bioassay accuracy, precision, and sensitivity.

DETAILED DESCRIPTION OF THE INVENTION

Figure 1:
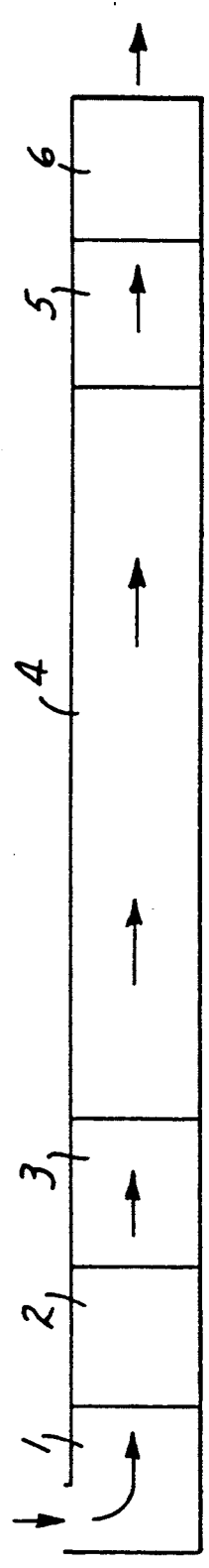
FIG. 1 is an exemplary flow diagram of a process for preparing the graft copolymers of the invention and those used in the compositions of the invention. Ancillary equipment known to those skilled in the art, such as pumps and valves, has not been illustrated, and secondary process streams such as utility lines (e.g., cooling water) have been omitted.

A graft copolymer of the invention comprises a poly-alpha-olefin base polymer and a monomer grafted thereto via an alkenyl group. The double bond is of course not present in the product graft copolymer; rather, in the grafting process the alkenyl group becomes a saturated (e.g., alkylene) link between the base polymer and the grafted moiety. In the instant specification and claims a reference to a grafted alkenyl group designates such a saturated link and does not designate the presence of olefinic unsaturation in the grafted monomer as it is incorporated in the graft copolymer.

Suitable base polymers include poly-alpha-olefins selected from the group consisting of polyethylene, polypropylene, polystyrene, and a compatible mixture of any two or more thereof. Base polymers of virtually any molecular weight are suitable. Likewise, base polymers and compatible mixtures thereof with a wide range of melt index values (e.g., from about 0.1 to about 1500) are suitable.

The olefinic monomer is selected from the group consisting of: in the instance of a polyethylene (PE) base polymer, 1-vinylimidazole (VIm), a polyethylene glycol monomethacrylate (PEG; polyethyleneglycol monomethacrylates of virtually any molecular weight, e.g., in the range from about 200 to about 10,000 are suitable), N-vinylpyrrolidone (NVP), and a mixture of any two or more thereof; in the instance of a polypropylene (PP) base polymer, 1-vinylimidazole; in the instance of a polystyrene (PS) base polymer, 1-vinylimidazole; and in the instance of a base polymer mixture of any two or more of polyethylene, polypropylene, and polystyrene, 1-vinylimidazole.

A graft copolymer of the invention comprises an amount of the grafted monomer effective to increase the amount of protein that will bind to the graft copolymer as compared with the base polymer. Stated another way, the graft copolymer binds proteins to a greater degree than does the base polymer. The amount that constitutes an effective amount of the grafted moiety will depend upon the particular grafted monomers and the particular base polymer. Generally, however, a graft copolymer comprises about 0.01% to about 20%, preferably 0.5 to about 10% by weight of grafted monomer. In the preparation of the graft copolymers (described in detail below) it is preferred to use like quantities of monomer, i.e., preferably about 0.01 to about 20% or more by weight, more preferably 0.5 to about 10% by weight based on the weight of the base polymer.

In a graft copolymer/protein composition of the invention, different grafted monomers are suitable depending on the particular base polymer. In the instance of a polyethylene base polymer, the grafted monomer is selected from the group consisting of 1-vinylimidazole, hydroxyethyl methacrylate (HEMA), N,N-dimethylacrylamide (DMA), polyethyleneglycol monomethacrylate, N-vinylpyrrolidone, and a mixture of any two or more thereof. In the instance of a polypropylene or polystyrene base polymer, and in the instance of a compatible base polymer mixture of any two or more of polyethylene, polypropylene, polystyrene, the grafted monomer is 1-vinylimidazole.

A graft copolymer used in a graft copolymer/protein composition of the invention, like a graft copolymer of the invention, comprises an amount of the grafted monomer effective to increase the amount of protein that will bind to the graft copolymer as compared with the base polymer. The amount that constitutes an effective amount is as discussed above in connection with graft copolymers of the invention.

In order to prepare a graft copolymer, the base polymer and the monomer are reacted in the presence of an initiator system comprising one or more free radical initiators. The initiator system serves to initiate free radical grafting of the monomer. In a process involving a base polymer that does not undergo substantial cross-linking under polymer melt conditions in the presence of a free radical initiator, the base polymer is degraded in the reactor. However, the selection of an appropriate initiator system affords a product graft copolymer that better retains the molecular weight of the base polymer.

Many initiators are known. Suitable initiators include: hydroperoxides such as cumene, t-butyl, and t-amyl hydroperoxides, and 2,5-dihydroperoxy-2,5-dimethylhexane; dialkyl peroxides such as di-t-butyl, dicumyl, and t-butyl cumyl peroxides, 2,5-dimethyl-2,5-di(t-butylperoxy)hexane, and 2,5-dimethyl-2,5-di(t-butylperoxy)hex-3-yne; peroxyesters such as t-butyl perbenzoate and di-t-butyl-diperoxy phthalate, diacyl peroxides such as benzoyl peroxide and lauroyl peroxide; peroxyketals such as n-butyl-4,4-bis(t-butylperoxy)-valerate and 1,1-di-t-butylperoxy-3,3,5-trimethylcyclohexane; and azo compounds such as azoisobutyronitrile.

The reaction conditions under which a graft copolymer is prepared typically involve heating at about 150° C. to about 250° C. The reactants typically have a residence time of about 1 to about 20 min. It is therefore difficult to select a single initiator with a decomposition rate such that initiating radicals will be present in a substantial concentration for a prolonged period of time when a relatively low concentration of initiator is used. It is therefore preferred to use a mixture of at least two initiators as an initiator system.

Proper selection of the components of the initiator system overcomes the above-discussed difficulty with single initiators, and allows control and optimization of the physical properties of the product graft copolymer. Generally it is preferred that each initiator in an initiator system have a rate of decomposition substantially different from those of the other initiators in the initiator system. For example, in a process with a residence time of about 5-10 minutes at a temperature of about 200° C., an initiator system wherein one initiator has a half-life of about 30 seconds and the other initiator has a half-life of about 2 minutes has been found to be suitable.

Preferred initiator systems include mixtures comprising from about 40% to about 60% by weight of 2,5-dimethyl-2,5-di(t-butylperoxy)hexane, (such as that commercially available as LUPERSOL TM 101 from Pennwalt Corporation) and from about 60% to about 40% by weight of an initiator such as 2,5-dimethyl-2,5-di(t-butylperoxy)hex-3-yne, (such as that commercially available as LUPERSOL TM 130 from Pennwalt Corporation), t-butylhydroperoxide, or di-t-butylperoxide. Initiator decomposition rates are temperature dependent, and other particular initiator systems and preferred concentration thereof can be selected by those skilled in the art consistent with the temperature of the reaction and the residence time of the reactants.

The total initiator concentration is preferably from about 0.1% to about 1%, more preferably from about 0.25% to about 0.5% based on the weight of the base polymer.

The graft copolymers can be prepared using various well known reactors such as stirred tank reactors, tubular reactors, and extruders. The graft copolymers are preferably made by a process involving a wiped-surface reactor. A wiped-surface reactor comprises a shell or vessel that contains at least one rotor having a wiping portion located close to the inside surface of the shell and a root portion that is spaced substantially further from the shell than the wiping portion. As the rotor is rotated, the wiping portion passes close enough to the inside surface of the shell to clean the surface and form a seal when the reactor contains monomer and/or polymer but not so close as to cause permanent deformation of either the rotor or shell. It is necessary that the root surface of the rotor also be wiped or cleaned continuously during the operation of the reactor.

Intermeshing twin screw extruders can be used as wiped-surface reactors. The screws function as the rotors and the flight lands function as the wiping portion, while the screw root surface between the flight lands functions as the root surface. Clearances between the inside of the barrel wall of the extruder and the flight lands of the screws are preferably in the range of about 0.25 to 0.5 mm. Although co-rotating twin screw extruders can be used, counter-rotating twin screw extruders are preferred. The counter-rotating extruder acts as a positive displacement pump conveying the reactant stream, and it also behaves like a series of small mixing zones or continuous stirred tank reactors. The counter-rotating twin screw extruder also gives good control over melting, mixing, and reaction temperatures.

Preferably, the screws of a counter-rotating twin screw extruder are divided into segments, i.e., the extruder screws can be composed of a number of separate screw segments that fit onto a common drive shaft by means of a keyway and can be disassembled and rearranged in various orders and configurations. It is also possible to utilize screw segments having multiple (e.g., two or three) starts and various pitch, and one or more screw segments can be reversed in order to increase mixing. Residence time of the reactants, and thus the properties of the resultant product, can therefore be varied by selection of screw pitch and/or screw speed (i.e., screw rpm). Furthermore, each particular zone of a twin screw extruder can be independently heated or cooled by external heating or cooling means, allowing further control of reaction conditions.

The use of a wiped-surface reactor is discussed with reference to FIG. 1. The base polymer can be fed in a region of the reactor coincident with the region in which the initiator system is fed. For example, the desired base polymer, preferably in pellet form, can be wetted with a free radical initiator system and purged with an inert gas such as nitrogen, helium, argon or the like, to render the material substantially free of oxygen (i.e., oxygen, if present, is present in an amount such that it does not significantly affect the desired free radical polymerization reactions). It is preferred to carry out the reaction under anhydrous conditions.

The base polymer/initiator mixture can be fed at a predetermined rate into feed zone 1 of the wiped-surface reactor. It is preferred, however, to feed the base polymer in a region of the reactor prior to or coincident with the region in which the initiator system is fed. Preferably, in instances where the base polymer is a poly-alpha-olefin that does not undergo substantial crosslinking under polymer melt conditions in the presence of a free radical initiator, the base polymer is fed to the reactor in a region of the reactor preceding or coincident with the region in which the initiator system is fed, and the monomer is fed to the reactor in a region of the reactor subsequent to the region in which the initiator is fed. In instances where the poly-alpha-olefin base polymer undergoes substantial crosslinking under polymer melt conditions in the presence of a free radical initiator, the base polymer and the initiator are preferably fed to the reactor in a region preceding the region in which the monomer is fed, but at a temperature such that crosslinking of the base polymer is minimized or prevented prior to the addition of the monomer.

The feed zone 1 typically comprises a feed throat, into which the base polymer can, if desired, be fed into the upstream end, and into which the initiator system can be fed at the downstream end. A further alternate method of feeding the base polymer and the initiator involves the use of a 2-component feed zone consisting of a base polymer feed zone into which the base polymer is fed, followed in sequence by a separate initiator feed zone into which the initiator is fed. The extruder is preferably starve fed, i.e., all material fed into the feed zone is conveyed into initiation/melt zone 2 of the extruder, and nothing is held up in the feed zone 1. Feed rates can vary with the size of the reactor and for any given size of reactor, one skilled in the art will be able to determine suitable feed rates. As an example, when a LEISTRITZ ™ 34 mm counter-rotating twin screw extruder is used feed rates are preferably from about 0.4 Kg/h to about 9 Kg/h. The feed zone screw preferably has a high pitch (e.g., 20 mm) to accommodate base polymer pellets. The feed zone can, if desired, be operated in a temperature controlled manner, depending on the reactants, reaction conditions and the like. Generally, it is suitable to maintain the feed zone of the extruder in a temperature range from about 10° C. to about 50° C., depending on the base polymer used.

In initiation/melt zone 2, the initiator system and the base polymer are mixed and heated. When non-crosslinking base polymers such as polypropylene and polystyrene are used, the temperature is preferably such that radical chain reactions are initiated. Preferred temperatures will depend on the particular base polymer and initiator system, but generally temperatures in the range between 150° C. and about 250° C. are suitable. When crosslinking base polymers such as polyethylene are used, both the feed zone and the initiation/melt zone are preferably kept at a temperature such that the initiator does not produce initiating radicals at a significant rate. As the residence time of the materials in these zones is only a small fraction of the total residence time, this serves to minimize or prevent the crosslinking of the base polymer prior to addition of the monomer. Again preferred temperatures will depend on the particular base polymer and initiator system. Generally, however, temperatures between about 100° C. and 150° C. are preferred.

In monomer addition zone 3, a nitrogen-purged monomer is added, usually by means of a high pressure pump and under an inert atmosphere. The monomer is generally fed as a liquid or as a solution in an inert solvent (e.g., decane, toluene, tetrahydrofuran or the like). Again, feed rates are variable, and when a LEISTRITZ ™ 34 mm counter-rotating twin screw extruder is used, feed rate is preferably about 4 g/h to about 180 g/h. It is preferred to maintain the monomer addition zone at a temperature of about 150° C. to about 250° C.

Grafting proceeds in reaction zone 4. The reaction zone is heated. The preferred temperature will depend on the particular base polymer and initiator system used. Further, the preferred temperature of the reaction zone will depend on the intended residence time in the reaction zone. Generally, temperatures in the range of 150° C. to 250° C. and residence times in the range of 1 minute to 10 minutes are suitable.

In reactions where there remains residual monomer, it is preferred to remove the residual monomer from the product by venting. This can be done in devolatilization zone 5, where a vacuum (e.g., about 10 kPa absolute pressure) can be applied to a vent line. The resultant product is passed through block zone 6, which conveys the product graft copolymer for any further processing as desired, e.g., shaping in a die, extruding, quenching in a suitable quenching liquid, or pelletizing to useful dimensions for convenience of handling and/or storage.

In instances where it is desirable to quench the graft copolymer in a quenching liquid, any suitable quenching liquid can be used. Water is commonly used. However, quenching in water can cause some undesirable hydrolysis of grafted hydrolytic moieties (if any), such as esters that will be present in graft copolymers wherein polyethyleneglycol monomethacrylate or hydroxyethyl methacrylate are the grafted monomers. Further, quenching in water can cause the graft copolymer to have a relatively high moisture content, which can cause internal hydrolysis of hydrolytic groups (if any) and poor performance of the graft copolymer upon molding. Therefore, it is preferred to quench the graft copolymer in a quenching liquid that is inert to any functional groups present in the monomer. It is also desirable for such a quenching liquid to have low volatility and a high specific heat. Suitable quenching liquids can be easily selected by those skilled in the art. Particularly preferred quenching liquids include inert liquid fluorocarbons.

A graft copolymer surface can bind (i.e., immobilize) proteins. The protein can be, for example, an antibody such as anti-human IgE, a protein such as Protein A, or an enzyme. Preferred proteins for immobilization include those with a molecular weight of at least 1000, most preferably at least about 4000.

A graft copolymer can be prepared, for example, in the form of an article such as a microtiter well or a test tube or in the form of beads or a film. To bind (i.e., immobilize) a protein to the surface of the article, the article can be contacted, e.g., incubated, with a protein, e.g., a serum or other solution containing a protein. The protein can also, if desired, contain a trace level of labeled (e.g., radiolabeled or fluorescence-labeled) protein to allow assay of the protein. An article with a protein bound thereto can then be further incubated, for example, with a relatively concentrated second protein solution such as bovine serum albumin, to block any remaining surface of the article and to displace initially adsorbed protein from the surface of the article.

An article treated as described above can be treated (e.g., incubated) with a protein denaturing agent such as sodium dodecylsulfate (SDS) to remove loosely-bound protein from the surface. Analysis of the resulting article shows that the amount of protein that is retained on the graft copolymer surface is increased by the grafted moiety.

The increased amount of irreversible binding of proteins such as antibodies in the graft copolymer/protein compositions of the invention suggests utility in applications where protein immobilization is desirable, e.g., diagnostic applications in which proteins are immobilized, including microtiter well assay devices, bead suspensions, and the like for use in ELISA and other well known enzyme immunoassay techniques such as those described in Clin. Chem. 1976, 22, 1263 (Wisdom). Furthermore, it is known that a proteinaceous layer will promote binding of cells to hydrophobic and hydrophilic base polymers. This invention allows one to immobilize proteins such as albumins, collagens, basement membrane fractions, etc., or specific proteins such as fibronectin, laminin, monoclonal antibodies, or adhesion proteins, etc., all of which can promote binding of cells to a polymer surface.

The immobilization of a protein on a graft copolymer can be carried out by contacting the protein with a graft copolymer surface at a temperature and for a time sufficient to cause the protein to bind to the graft copolymer surface. While it is not practical to enumerate particular conditions suitable for each and every protein, such conditions can be easily selected by those skilled in the art. Generally, however, room temperature exposure of a graft copolymer surface to a solution of the protein in an appropriate solvent will be suitable to bind the protein to the surface.

The amount of grafted moieties on the surface of a graft copolymer can be measured by conventional means such as x-ray photoelectron spectroscopy, Fourier transform infrared spectrophotometry, attenuated total reflectance infrared spectrophotometry, and the like.

The following describes the preparation of graft copolymers and graft copolymer/protein compositions. Temperatures are in degrees Celsius, and all parts and percentages are by weight. Graft copolymers are designated herein by enumerating the base polymer and the grafted monomer, e.g., the designation PE/DMA represents a graft copolymer comprising a polyethylene (PE) base polymer having N,N-dimethylacrylamide (DMA) grafted thereto.

Intermediate A

Preparation of polyethylene (PE)/hydroxyethyl methacrylate (HEMA).

HEMA was grafted onto linear low-density PE (DOWLEX TM 2517, melt index:25, Dow Chemical Co.,.Midland, MI) using a counter-rotating 34 mm LEISTRITZ TM twin-screw extruder model LSM 30.3466, (Nuremburg, Germany), with a length:diameter ratio at 35:1, configured as described below with reference to FIG. 2.

Figure 2:
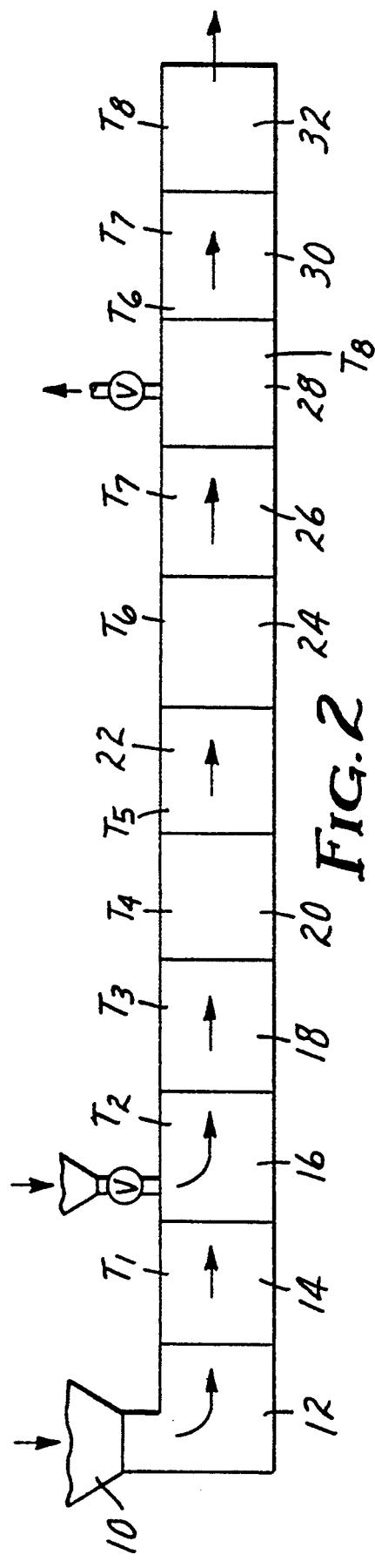
FIG. 2 is a flow diagram of a counter-rotating twin screw extruder useful in preparing graft copolymers.

FIG. 2 shows a twin-screw extruder with a feed hopper 10, feed zone 12, and a heated barrel that comprises: an initiation/melt zone comprising barrel section 14; a reaction zone comprising a monomer feed zone (barrel section) and barrel sections 18, 20, 22, 24, and 26; a devolatilization zone comprising barrel section 28; and a block zone comprising barrel sections 30 and 32. Each barrel section is 120 mm long, and the extruder has a total length of 1200 mm.

Transducer ports (e.g., T4 represents transducer number 4 located in barrel section 24) are located at 30 mm, and/or 90 mm into each heated barrel section. Thermocouple ports are located at 60 mm into each heated barrel section.

The polyethylene base polymer was directly fed into the feed throat. A 1:1 mixture by weight of LUPERSOL TM 101 and LUPERSOL TM 130 was fed at 4.1 mL/h, and a 1:1 mixture by weight of LUPEROX TM 500 dicumyl peroxide (Pennwalt) and decane was also fed at 4.2 mL/h, each to the feed throat and each by a separate nitrogen purged RUSKA TM pump. The HEMA was purged with nitrogen, added to a nitrogen-purged RUSKA TM positive displacement pump, and added at a rate of 160 mL/h in heated barrel section 16, 270 mm from the start of the screws. Total flow rate was 40 g/min. Screw speed was 103 rpm. The temperature profile was as follows: Section 14, 253°; Section 16, 145°; Section 18, 181°; Section 20, 199°; Section 22, 201°; Section 24, 197°; Section 26, 205°; Section 30, 234°; Section 32, 205°; Section 34, 202°. In heated barrel section 28 residual monomer was removed by vacuum. The product graft copolymer was conveyed from the block zone (barrel sections 30 and 32), into a water bath and fed into a Conair Co. (Bay City, Michigan) pelletizer to afford generally cylindrical beads of 3–4 mm in length and about 1 mm in diameter. The melt index of the product graft copolymer was 18 as measured by ASTM D-1238, indicating that crosslinking of the polyethylene occurred during the grafting process.

Intermediate B and Examples 1–3

Preparation of PE/NVP (Intermediate B), PE/VIm, PP/VIm, and PE/PEG.

PE (DOWLEX TM 2517) and PP (DYPRO TM 8771) were independently used as base polymers, and NVP, polyethyleneglycol monomethacrylate (SIPO-MER TM HEM-10 Alcolac), and VIm (Aldrich Chem. Co.) were independently used as monomers. Graft copolymers were prepared in a LEISTRITZ TM 34 mm twin-screw extruder as generally described above in connection with Intermediate A. The monomer was purged with nitrogen gas for 15–30 min prior to use. The feed hopper and feed throat of the extruder were kept under nitrogen gas throughout. The monomer was injected into the second zone of the extruder via a RUSKA TM single-piston positive-displacement pump at a pressure of 50 psi. The initiator (a 1:1 mixture of LUPERSOL TM 101 and LUPERSOL TM 130) was fed into the open feed throat via a dual-piston RUSKA TM pump. The extruded graft polymer was formed into a strand, quenched, and pelletized. Other conditions are listed in Table 1 below.

TABLE 1

| | Polymerization Conditions | | | |
| | Graft Copolymer | | | |
| Condition | PE/VIm Ex. 1 | PP/VIm Ex. 2 | PE/NVP Int. B | PE/PEG Ex. 3 |
|---|---|---|---|---|
| Screw speed (rpm) | 85 | 100 | 100 | 100 |
| Temperature (°C.) | | | | |
| Section | | | | |
| 14 | 154 | 195 | 153 | 150 |

TABLE 1-continued

| | Polymerization Conditions | | | |
| | | Graft Copolymer | | |
| Condition | PE/VIm Ex. 1 | PP/VIm Ex. 2 | PE/NVP Int. B | PE/PEG Ex. 3 |
| --- | --- | --- | --- | --- |
| 16 | 150 | 199 | 147 | 150 |
| 18 | 165 | 204 | 157 | 160 |
| 20 | 163 | 200 | 159 | 160 |
| 22 | 160 | 197 | 157 | 160 |
| 24 | 154 | 195 | 153 | 160 |
| 26 | 158 | 202 | 161 | 160 |
| 28 | 185 | 215 | 184 | 160 |
| 30 | 161 | 204 | 163 | 160 |
| 32 | 161 | 182 | 163 | 160 |
| Polymer flow (g/min) | 39 | 42.1 | 42.9 | 42 |
| Init. flow (mL/h) | 3.0 | 8.9 | 3.0 | 8.9 |
| Initiator Percent | 0.1 | 0.3 | 0.1 | 0.3 |
| Monomer flow (mL/h) | 30 | 120 | 120 | 160 |
| Percent Incorporated Monomer | 0.17 | 3.2 | 1.9 | 3.1 |

Intermediate C

Preparation of PE/DMA.

A graft copolymer was prepared in a Brabender Plasti-corder reactor, type EPL-V5501, (C. W. Brabender Co.), equipped with a type RE.E.6 mixing head, a type SP-T1002 temperature control console, and a torque rheometer. The reactor was preheated to 180° C. under a nitrogen purge. PE (DOWLEX TM 2517) was used as base polymer. N,N-Dimethylacrylamide (DMA, Aldrich Chemical Co.) was used as the monomer. The base polymer (45 g) was added to the reactor and mixed at 30 rpm until fully melted. The initiator (0.14 g of a 1:1 mixture of LUPERSOL TM 101/LUPERSOL TM 130) was added to the polymer and allowed to mix for about one-half minute. DMA (2.4 g; 5 weight percent) was added to the mixture and allowed to react for 3 minutes. The mixture was removed from the reactor and cooled to ambient temperature. The PE/DMA contained 0.25% DMA by weight. Cooled samples were stored in plastic bags until use.

Example 4

Preparation of PS/VIm.

According to the general method of Intermediate C, polystyrene (39 g, Polysar TM 101-300, melt index 2.2, Polysar Inc., Leominster, Massachusetts) and 1-vinylimidazole (1.0 g) were reacted to afford PS/VIm.

Examples 5–11

The immobilization of protein on PE, PP, PS, and their graft copolymers.

Film samples of the graft copolymer with thickness of about 0.13 mm were made by pressing (at a pressure of about 41.4 kPa for 30 seconds using a WABASH TM heated press, Wabash, Indiana) about 10 g of the graft copolymer between TEFLON TM plates at about 200° C. Pressed samples were quenched from the molten state to the solid state in a room temperature water bath and cut into discs of 8 mm diameter using a conventional paper punch. Recombinant Protein A (rProtA), purchased from Repligen (Cambridge, Massachusetts), was radioiodinated using Iodo-beads TM (Pierce Chemical Co., Rockford, Illinois). rProtA (200 μL of 250 μg/mL), with a specific radioactivity of 2000 cpm/μg of protein, was incubated with triplicate samples of 8 mm film discs in 25 mM sodium phosphate, pH 7.5, with 150 mM sodium chloride. Incubations were terminated after 2 h by removal of the solution followed by addition of 500 μL of 1.0 M ethanolamine, pH 9.0, for 1 h. Finally, the film discs were rinsed three times with the chloride-phosphate buffer for 45 minutes, then transferred to a clean tube for radioactivity determination using a Packard Model 5230 Gamma Scintillation Spectrometer (Packard Instrument Co., Downers Grove, Illinois). The film discs were subsequently incubated for 4 h at 37° with an aqueous solution of 1% w/v sodium dodecylsulfate (SDS), rinsed three times with the same SDS solution, followed by a final radioactivity determination.

TABLE 2

Comparative Binding of Protein on Control and Grafted Polymers

| Example | Polymer | Adsorbed Protein (μg/cm$^2$) | SDS Resistance | Tightly Bound Protein (μg/cm$^2$) |
| --- | --- | --- | --- | --- |
| | PE | 0.51 | 22% | 0.11 |
| 5 | PE/VIm | 1.12 | 40 | 0.46 |
| 6 | PE/HEMA | 0.77 | 32 | 0.25 |
| 7 | PE/DMA | 0.88 | 27 | 0.23 |
| 8 | PE/NVP | 0.81 | 31 | 0.24 |
| | PE* | 0.44 | 19 | 0.08 |
| 9 | PE/PEG* | 0.54 | 53 | 0.29 |
| | PP | 0.90 | 24 | 0.22 |
| 10 | PP/VIm | 1.04 | 28 | 0.29 |
| | PS* | 1.40 | 28 | 0.39 |
| 11 | PS/VIm* | 2.34 | 50 | 1.16 |

*Protein A solution had specific radioactivity of 2250 cpm/μg

The amount of protein bound to the base polymers increased in the order of the increasing hydrophobicity of the base polymer, i.e., PS > PP > PE. All grafted monomers enhanced the binding of protein relative to base polymer surfaces. All the graft copolymers had increased SDS resistance compared with the base polymer.

Examples 12–16

Stability of protein adsorbance in the presence of blood proteins.

Protein incubation was carried out as described in Examples 5–9 above. The specific radioactivity of rProtA was 1360 cpm/μg. After the initial radioactivity determination the films were incubated for 7 days at ambient temperature with 500 μL of a 1:1 buffer:human serum solution. Residual radioactivity was determined following the incubation, aspiration of the serum solution, and two buffer rinses. The films were subjected to the SDS treatment described in Examples 5–9, and a final radioactivity determination was made. The results are set forth in TABLE 3 below.

TABLE 3

The Effect of Long-Term Incubation of Protein-Bound Films in Serum

| Example | Polymer | Adsorbed Protein | Post-plasma Adsorbance | SDS Resistance | Covalent Protein |
| --- | --- | --- | --- | --- | --- |
| | PE | 0.64 μg/cm$^2$ | 0.22 μg/cm$^2$ | 6% | 0.04 μg/cm$^2$ |
| 12 | PE/VIm | 1.60 | 0.89 | 33 | 0.53 |
| 13 | PE/HEMA | 1.06 | 0.48 | 19 | 0.20 |

TABLE 3-continued

The Effect of Long-Term Incubation of Protein-Bound Films in Serum

| Example | Polymer | Adsorbed Protein | Post-plasma Adsorbance | SDS Resistance | Covalent Protein |
|---------|---------|------------------|------------------------|----------------|------------------|
| 14      | PE/DMA  | 1.04             | 0.41                   | 6              | 0.07             |
| 15      | PE/NVP  | 1.08             | 0.34                   | 6              | 0.06             |
|         | PP      | 1.18             | 0.39                   | 10             | 0.12             |
| 16      | PP/VIm  | 1.45             | 0.66                   | 15             | 0.23             |

Treatment with plasma proteins followed by SDS treatment is a stringent test to remove proteins from a surface. Surprisingly, three of the polymers (PE/VIm, PE/HEMA, PP/VIm) contained residual, tightly-bound protein.

The claimed invention is:

1. A graft copolymer consisting essentially of a uniform, homogeneous thermoplastic of
   i) polyethylene and
   ii) an amount of a grafted monomer selected from the group consisting of 1-vinylimidazole, hydroxyethyl methacrylate, polyethylene glycol monomethacrylate, N-vinyl pyrrolidone, N,N-dimethylacrylamide and mixtures thereof effective to increase protein binding to the graft copolymer as compared with polyethylene.

2. The graft copolymer of claim 1 wherein the graft copolymer comprises about 0.01-20.0 wt. % grafted monomer.

3. The graft copolymer of claim 1 wherein the graft copolymer comprises about 0.5-10.0 wt. % grafted monomer.

4. The graft copolymer of claim 1 in the form of a microtiter well, a test tube, a bead, or a film.

5. A graft copolymer consisting essentially of a uniform, homogeneous thermoplastic of:
   i) a base polymer selected from the group consisting of polypropylene, polystyrene, and mixtures thereof and
   ii) an amount of 1-vinylimidazole effective to increase protein binding to the graft copolymer as compared with protein binding to only the base polymer, wherein the base polymer is selected from the group consisting of polypropylene, polystyrene, and mixtures thereof.

6. The graft copolymer of claim 5 wherein the graft copolymer comprises about 0.01-20.0 wt. % grafted monomer.

7. The graft copolymer of claim 5 wherein the graft copolymer comprises about 0.5-10.0 wt. % grafted monomer.

8. The graft copolymer of claim 5 in the form of a microtiter well, a test tube, a bead, or a film.

* * * * *

UNITED STATES PATENT AND TRADEMARK OFFICE
CERTIFICATE OF CORRECTION

PATENT NO. : 5,364,907
DATED : November 15, 1994
INVENTOR(S) : Richard J. Rolando, Patrick L. Coleman, Steven L. Kangas, and Thomas A. Kotnour It is certified that error appears in the above-indentified patent and that said Letters Patent is hereby corrected as shown below:

Col. 1, line 27    "(Else et al.)" should read --(Eise et al.)--

Col. 12, line 21   insert as new paragraph --The results are shown in Table 2.--

Signed and Sealed this

Nineteenth Day of September, 1995

Attest:

BRUCE LEHMAN

*Attesting Officer*     *Commissioner of Patents and Trademarks*